United States Patent [19]

Tanner et al.

[11] Patent Number: 4,985,238

[45] Date of Patent: Jan. 15, 1991

[54] LOW RESIDUE ANTIPERSPIRANT STICKS

[75] Inventors: Paul R. Tanner; Randolph G. Nunn, Jr., both of Cincinnati, Ohio; John P. Luebbe, Lawrenceburg, Ind.

[73] Assignee: The Procter & Gamble Company, Cincinnati, Ohio

[21] Appl. No.: 323,523

[22] Filed: Mar. 14, 1989

[51] Int. Cl.$^5$ .................. A61K 7/32; A61K 7/34; A61K 7/36; A61K 7/38

[52] U.S. Cl. .................. 424/66; 424/DIG. 5; 424/67; 424/68

[58] Field of Search .................. 424/66, DIG. 5, 68

[56] References Cited

U.S. PATENT DOCUMENTS

| | | | |
|---|---|---|---|
| 3,255,082 | 6/1966 | Barton et al. | 424/68 |
| 3,968,203 | 7/1976 | Spitzer et al. | 424/47 |
| 4,083,956 | 4/1978 | Shelton | 424/66 |
| 4,229,432 | 10/1980 | Geria | 424/68 |
| 4,265,878 | 5/1981 | Keil | 424/68 |
| 4,425,328 | 1/1984 | Nabial | 424/68 |
| 4,724,139 | 2/1988 | Palinczar | 424/66 |
| 4,840,789 | 6/1989 | Orr et al. | 424/66 |
| 4,863,721 | 9/1989 | Beck et al. | 424/66 |

FOREIGN PATENT DOCUMENTS 28853 5/1981 European Pat. Off. ............ 424/66

OTHER PUBLICATIONS

Ser. No. 323,524, 3/14/89, Patent Application, Tanner et al.

Primary Examiner—Dale R. Ore
Attorney, Agent, or Firm—Steven J. Goldstein; Gretchen R. Hatfield; Richard C. Witte

[57] ABSTRACT

Suspensoid antiperspirant stick compositions, which provide the user with excellent antiperspirant efficacy, reduced residue upon application to the skin, reduced residue on the stick after dry-down, and excellent cosmetics and aesthetics, are disclosed. These compositions are substantially free of water and comprise a volatile silicone material, a particulate antiperspirant active, a low melting point wax, and a non-volatile paraffinic hydrocarbon fluid selected from mineral oils and branched chain $C_{16}$-$C_{68}$ hydrocarbons. The method of preventing and controlling perspiration wetness using these compositions is also disclosed.

11 Claims, No Drawings

LOW RESIDUE ANTIPERSPIRANT STICKS

TECHNICAL FIELD

The present invention relates to antiperspirant sticks, substantially free of water, which provide the user with excellent antiperspirant efficacy, reduced residue when the composition is first applied to the skin, reduced residue on the skin after dry down, high temperature stability, and excellent cosmetics and aesthetics.

BACKGROUND OF THE INVENTION

Many solid antiperspirant compositions have been described in the chemical and cosmetic literature. These compositions generally tend to fall into one of two classes: emulsion sticks and suspensoid sticks. Emulsion sticks contain a solution of the antiperspirant active incorporated into the stick via an emulsion. Although emulsion sticks may be desirable in certain respects, they tend to be unstable, have poor aesthetics (e.g., are overly hard, greasy or sticky), and leave a visible residue on the skin after use. Suspensoid sticks contain the powdered antiperspirant active suspended in the stick without the use of water or an emulsion. While suspensoids tend to be stable, they may be brittle and hard and, more importantly, they tend to leave an unsightly white chalky residue on the skin after application. This residue is not only aesthetically displeasing to the user, but can also soil clothing. It has now been discovered that when certain non-volatile paraffinic hydrocarbon fluids, such as mineral oils or branched chain $C_{16}$-$C_{68}$ hydrocarbons, are incorporated into water-free suspensoid antiperspirant stick compositions, those compositions exhibit excellent antiperspirant efficacy and aesthetics, while leaving reduced visible residue on the skin of the user. The present invention may also provide a benefit in terms of improved delivery and substantivity of perfumes included in the compositions.

Although mineral oil and some volatile branched chain hydrocarbons have been taught for use in certain types of deodorant compositions, they have not heretofore been taught for use in substantially water-free suspensoid type stick compositions. For example, mineral oil has been used in water-containing emulsion type deodorant sticks (see, e.g., U.S. Pat. No. 3,255,082, Barton et al., issued June 7, 1966), in aerosol deodorants (e.g., U.S. Pat. No. 3,968,203, Spitzer et al., issued July 6, 1976), and in deodorant creams (see, e.g., U.S. Pat. No. 4,083,956, Shelton, issued April 11, 1978). See also European Patent Application 28,853, Beckmeyer et al., published May 20, 1981 (mineral oil as a non-volatile emollient in liquid antiperspirant compositions).

U.S. Pat. No. 4,425,328, Nabial, issued January 19, 1984, describes deodorant sticks containing an antiperspirant active, a volatile cyclic silicone emollient, a clay suspending agent, and an activator for the clay. These compositions may optionally include emollients, such as 2-ethyl hexyl palmitate. U.S. Pat. No. 4,265,878, Keil, issued May 5, 1981, describes emulsion type deodorant sticks containing an antiperspirant active dispersed in a solid matrix which includes a volatile water-insoluble liquid. Useful volatile liquids include cyclic polysiloxanes and volatile paraffinic hydrocarbons, such as branched chain $C_{15}$ or lower hydrocarbons. U.S. Pat. No. 4,229,432, Geria, issued Oct. 21, 1980, describes the use of certain waxy materials (such as straight and branched-chain paraffinic hydrocarbon waxes) to keep active components dispersed in an antiperspirant stick. U.S. Pat. No. 4,724,139, Palinczar, issued Feb. 9, 1988, describes antiperspirant sticks which include 5–80% of a volatile isoparaffin liquid, 5–60% of a water-insoluble wax, and 8–60% of a particulate antiperspirant active. It is to be emphasized that the Keil and Palinczar products tend to be unacceptable in terms of visible residue on the skin after use, high temperature stability and/or aesthetics.

SUMMARY OF THE INVENTION

The present invention provides suspensoid low residue antiperspirant stick compositions, substantially free of water, which comprise:
(a) from about 30% to about 70% of a volatile silicone material;
(b) from about 5% to about 35% of a particulate antiperspirant active;
(c) from about 3% to about 20% of a non-volatile paraffinic hydrocarbon fluid selected from the group consisting of mineral oils, branched chain hydrocarbons containing an average of from about 16 to about 68 carbon atoms, and mixtures thereof; and
(d) from about 10% to about 20% of a low melting point wax.

DETAILED DESCRIPTION OF THE INVENTION

The antiperspirant compositions of the present invention are in solid stick form and they are suspensoids (i.e., the powdered antiperspirant active is suspended in the stick). The compositions, for stability reasons, are substantially free of water, by which it is meant that the compositions contain no more than about 5% water, preferably no more than about 2% water, and most preferably contain no water.

All percentages and ratios specified herein are by weight, unless otherwise specified.

The required, as well as the optional, components of the present invention are described in detail below.

Non-volatile Paraffinic Hydrocarbon Fluid

The compositions of the present invention include from about 3% to about 20%, preferably from about 5% to about 15%, of a non-volatile paraffinic hydrocarbon fluid. If the level of non-volatile hydrocarbon fluid is too low, the low residue benefits of the present invention are not seen; if the level of non-volatile hydrocarbon fluid is too high, the deodorant product tends to have too low a melting point to be useful. As used herein, the term "non-volatile" means that the hydrocarbon fluids used in the present invention have a boiling point of at least about 250° C. Further, the hydrocarbon fluids must be liquids at room temperature. The hydrocarbon fluids useful in the present invention include mineral oils and certain branched-chain hydrocarbons.

Mineral oils useful in the present invention are petroleum derivatives which are complex mixtures of paraffinic and naphthenic (cyclic) hydrocarbons. These include both "light" and "heavy" mineral oils, which are differentiated on the basis of the average molecular weight of the hydrocarbons included. The mineral oils useful herein have the following properties:
viscosity of from about 5 centistokes to about 70 centistokes at 40° C.;
density between about 0.82 and about 0.89 g/cm$_3$ at 25° C.;

flash point between about 138° C. and about 216° C.; and carbon chain length between about 14 and about 40 carbons.

The branched chain hydrocarbons useful in the present invention are highly branched non-volatile aliphatic liquids containing an average of from about 16 to about 68, preferably from about 20 to about 40, carbon atoms. If the compounds are not sufficiently branched, they will be waxes rather than the liquids required in the present invention. Materials containing 15 and fewer carbons tend to be too volatile for use in the present invention. Commercially available materials are mixtures of various branched chain compounds, rather than a single pure compound. Branched chain hydrocarbon fluids useful herein have the following properties:

density between about 0.79 and about 0.89 g/cm$^3$ at 20° C.;

boiling point greater than about 250° C.; and flash point between about 110 C. and about 200° C.

Preferred branched chain hydrocarbons are commercially available under the tradenames Permethyl (Permethyl Corporation) and Isopar (Exxon). In selecting a branched chain hydrocarbon material, its average carbon chain length, density, boiling point, and flash point must be considered to make certain that it falls within the ranges set forth herein. Particularly preferred materials include Permethyl 103A, which contains an average of about 24 carbon atoms, Permethyl 104A, which contains an average of about 68 carbon atoms, and Permethyl 102A, which contains an average of about 20 carbon atoms.

Antiperspirant Material

The present compositions contain from about 5% to about 35%, preferably from about 10% to about 30%, by weight of a particulate antiperspirant material. These weight percentages are calculated on an anhydrous metal salt basis (exclusive of glycine, the salts of glycine, or other complexing agents). The particulate antiperspirant material preferably has particle sizes ranging from about 1 to about 100 microns, more preferably from about 1 to about 50 microns. They may be impalpable or microspherical in form and, preferably, have a high bulk density (e.g., greater than about 0.7 g/cm$^3$). Such materials include, for example, many aluminum or zirconium astringent salts or complexes and are well known in the antiperspirant art.

Any aluminum astringent antiperspirant salt or aluminum and/or zirconium astringent complex in particulate form can be employed herein. Salts useful as astringent antiperspirant salts or as components of astringent complexes include aluminum halides, aluminum hydroxyhalides, zirconyl oxyhalides, zirconyl hydroxyhalides, and mixtures of these salt materials.

Aluminum salts of this type include aluminum chloride and the aluminum hydroxyhalides having the general formula $Al_2(OH)_xQ_y \cdot XH_2O$ where Q is chlorine, bromine or iodine; where x is from about 2 to about 5, and x+y=about 6, and x and y do not need to be integers; and where X is from about 1 to about 6. Aluminum salts of this type can be prepared in the manner described more fully in U.S. Pat. No. 3,887,692, Gilman, issued June 3, 1975, and U.S. Pat. No. 3,904,741, Jones and Rubino, issued Sept. 9, 1975, incorporated herein by reference.

The zirconium compounds which are useful in the present invention include both the zirconium oxy salts and zirconium hydroxy salts, also referred to as the zirconyl salts and zirconyl hydroxy salts. These compounds may be represented by the following general empirical formula:

$$ZrO(OH)_{2-nz}B_z$$

wherein z may vary from about 0.9 to about 2 and need not be an integer, n is the valence of B, 2−nz is greater than or equal to O, and B may be selected from the group consisting of halides, nitrate, sulfamate, sulfate, and mixtures thereof. Although only zirconium compounds are exemplified in this specification, it will be understood that other Group IV B metal compounds, including hafnium, could be used in the present invention.

As with the basic aluminum compounds, it will be understood that the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amounts of the hydroxy group, varying from about 1.1 to only slightly greater than 0 groups per molecule.

Several types of antiperspirant complexes utilizing the above antiperspirant salts are known in the art. For example, U.S. Pat. No. 3,792,068, Luedders et al., issued Feb. 12, 1974, discloses complexes of aluminum, zirconium and amino acids such as glycines. Complexes such as those disclosed in the Luedders et al. patent and other similar complexes are commonly known as ZAG. ZAG complexes are chemically analyzable for the presence of aluminum, zirconium and chlorine. ZAG complexes useful herein are identified by the specification of both the molar ratio of aluminum to zirconium (hereinafter "Al:Zr" ratio) and the molar ratio of total metal to chlorine (hereinafter "Metal:Cl" ratio). ZAG complexes useful herein have an Al:Zr ratio of from about 1.67 to about 12.5 and a Metal:Cl ratio of from about 0.73 to about 1.93.

Preferred ZAG complexes are formed by
(A) co-dissolving in water
  (1) one part $Al_2(OH)_{6-m}Q_m$, wherein Q is an anion selected from the group consisting of chloride, bromide and iodide, and m is a number from about 0.8 to about 2.0;
  (2) x parts $ZrO(OH)_{2-a}Q_a \cdot nH_2O$, where Q is chloride, bromide or iodide; where a is from about 1 to about 2; where n is from about 1 to about 8; and where x has a value of from about 0.16 to about 1.2;

(3) p parts neutral amino acid selected from the group consisting of glycine, dl-tryptophane, dl-β-phenylalanine, dl-valine, dl-methionine and β-alanine, and where p has a value of from about 0.06 to about 0.53;
(B) co-drying the resultant mixture to a friable solid; and
(C) reducing the resultant dried inorganic-organic anti perspirant complex to particulate form.

A preferred aluminum compound for preparation of such ZAG type complexes is aluminum chlorhydroxide of the empirical formula $Al_2(OH)_5Cl \cdot 2H_2O$. Preferred zirconium compounds for preparation of such ZAG-type complexes are zirconyl hydroxychloride having the empirical formula $ZrO(OH)Cl \cdot 3H_2O$ and the zirconyl hydroxyhalides of the empirical formula ZrO(OH)-

$_{2-a}Cl_2.nH_2O$ wherein a is from about 1.5 to about 1.87, and n is from about 1 to about 7. The preferred amino acid for preparing such ZAG-type complexes is glycine of the formula $CH_2(HN_2)COOH$. Salts of such amino acids can also be employed in the antiperspirant complexes. See U.S. Pat. No. 4,017,599, Rubino, issued April 12, 1977, incorporated herein by reference.

A wide variety of other types of antiperspirant complexes are also known in the art. For example, U.S. Pat. No. 3,903,258, Siegal, issued Sept. 2, 1975, discloses a zirconium aluminum complex prepared by reacting zirconyl chloride with aluminum hydroxide and aluminum chlorhydroxide. U.S. Pat. No. 3,979,510, Rubino, issued Sept. 7, 1976, discloses an antiperspirant complex formed from certain aluminum compounds, certain zirconium compounds, and certain complex aluminum buffers. U.S. Pat. No. 3,981,896, issued Sept. 21, 1976, discloses an antiperspirant complex prepared from an aluminum polyol compound, a zirconium compound and an organic buffer. U.S. Pat. No. 3,970,748, Mecca, issued July 20, 1976, discloses an aluminum chlorhydroxy glycinate complex of the approximate general formula $[Al_2(OH)_4Cl][H_2CNH_2-COOH]$. All of these patents are incorporated herein by reference.

Of all the above types of antiperspirant actives, preferred compounds include the 5/6 basic aluminum salts of the empirical formula $Al_2(OH)_5Cl.2H_2O$; mixtures of $AlCl_3.6H_2O$ and $Al_2(OH)_5Cl. 2H_2O$ with aluminum chloride to aluminum hydroxychloride weight ratios of up to about 0.5; ZAG type complexes wherein the zirconium salt is $ZrO(OH)Cl.3H_2O$, the aluminum salt is $Al_2(OH)_5Cl. 2H_2O$ or the aforementioned mixtures of $AlCl_3.6H_2O$ and $Al_2(OH)_5Cl.2H_2O$ wherein the total metal to chloride molar ratio in the complex is less than about 1.25 and the Al:Zr molar ratio is about 3.3, and the amino acid is glycine; and ZAG-type complexes wherein the zirconium salt is $ZrO(OH)_{2-a}Cl_a.nH_2O$ wherein a is from about 1.5 to about 1.87 and n is from about 1 to about 7, the aluminum salt is $Al_2(OH)_5Cl.2H_2O$, and the amino acid is glycine.

The aluminum chlorhydrate (ACH) actives are particularly preferred for use in the present invention since they tend to leave less residue than other actives when applied to skin.

Volatile Silicone Material

Volatile silicones known for use in deodorant sticks are useful in the present invention. The volatile silicone component is preferably either a cyclic or a linear polydimethylsiloxane and is present at a level of from about 30% to about 70%, preferably from about 35% to about 50%, of the composition.

The cyclic polydimethylsiloxanes preferably have from about 3 to about 7 silicon atoms, more preferably from about 4 to about 5 silicon atoms.

The general formula for such silicones is

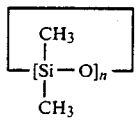

wherein n = 3 - 7

The linear polydimethylsiloxanes contain from about 3 to about 9 silicon atoms and have the general formula

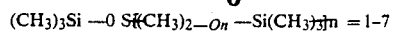

Silicones of the above type are commercially available, for example, from Dow Corning Corporation (Dow Corning 344, 345 and 200 fluids), Union Carbide (Silicone 7207 and Silicone 7158), and Stauffer Chemical (SWS-03314).

The linear volatile silicone materials generally have viscosities of less than about 5 centistokes at 25° C., while the cyclic materials have viscosities less than about 10 centistokes. "Volatile" means that the material has a measurable vapor pressure. A description of volatile silicones is found in Todd and Byers, "Volatile Silicone Fluids for Cosmetics", *Cosmetics and Toiletries*, 91:27-32 (1976), incorporated herein by reference.

Low Melting Point Waxes

The antiperspirant sticks of the present invention also contain one or more wax-like materials having a low melting point, i.e., having a melting point of from about 37° C. to about 75° C. These low melting point waxes are present at from about 10% to about 20% of the composition. Such materials are well known in the art and include fatty acids, fatty alcohols, fatty acid esters, and fatty acid amides, having fatty chains of from about 8 to about 30, preferably from about 12 to about 18, carbon atoms. Preferred low melting point waxes include cetyl alcohol, palmitic acid, myristyl alcohol, stearyl alcohol, paraffin, and mixtures thereof. Stearyl alcohol, cetyl alcohol, and mixtures thereof are particularly preferred.

Non-essential Components

The compositions of the present invention may also contain optional components which modify the physical characteristics of the compositions or serve as "active" components when deposited on the skin in addition to the particulate antiperspirant material. Examples of such additional actives include bacteriostats and fungistats. Optional components useful herein are described in the following documents, all incorporated by reference herein: U.S. Pat. No. 4,049,792, Elsnau, issued Sept. 20, 1977; Canadian Pat. No. 1,164,347, Beckmeyer et al., issued Mar. 27, 1984; European Patent Specification No. 117,070, May, published Aug. 29,1984; and Geria, "Formulation of Stick Antiperspirants and Deodorants", *Cosmetics & Toiletries*, 99:55-60 (1984).

The specific non-active components that may be useful will depend upon the characteristics desired for the particular stick composition. Such components include, for example, emollients, colorants, perfumes, and emulsifiers. Although the present compositions may also contain fillers and particulate materials (such as talc and silica (fumed and non-fumed)) other than the antiperspirant active described above, such particulates may adversely affect the perceived low residue benefits of the present invention. As used herein, "particulate materials" are those materials that neither dissolve in the composition components, nor melt during manufacture of the stick. Preferably, the compositions of the present invention contain a total level of particulate materials, other than the antiperspirant materials, of less than about 4%. More preferably, the present compositions contain less than about 3% of particulate materials other than the particulate antiperspirant material.

The antiperspirant sticks of the present invention may contain one or more materials having wax-like characteristics and a melting point of from about 65° C. to about 130° C. When used, these high melting point waxes are present at from about 1% to about 7% of the composition. Such waxes include beeswax, carnauba, baysberry, candelilla, montan, ozokerite, ceresin, hydrogenated castor oil (castor wax), synthetic waxes such as Fisher-Tropsch waxes, microcrystalline waxes, and mixtures thereof. Castor wax is a preferred high melting point wax for use herein. High melting point waxes useful in the present invention are disclosed in U.S. Pat. No. 4,049,792, Elsnau, issued Sept. 20, 1977, incorporated herein by reference.

Another optional component which may be used in the present invention is a finely divided silica material (called a "colloidal silica material") which is comprised of micron to sub-micron sized silica particulates with high surface area (preferably greater than about 100 square meters per gram of material). As discussed above, if used, the level of these particulate materials should be kept relatively low (e.g., from about 0.3% to about 1.5% of the composition) to avoid a negative impact on the low residue characteristics of the present invention. Colloidal silica materials useful herein include Syloid silicas (manufactured by Davison Chemical Division of W. R. Grace), Cab-O-Sil (manufactured by Cabot Corporation), and Aerosil (manufactured by Degussa A.G.). Cab-O-Sil, having a surface area of from about 200 to about 400 square meters per gram, is a particularly preferred commerciallyavailable colloidal silica useful herein.

The antiperspirant sticks of this invention may be manufactured using methods known in the art. Typically, all ingredients are combined and heated to a temperature of from about 70° C. to about 95° C. (depending upon the type and level of waxes, as well as other components, included in the compositions). The bulk composition is then cooled, with agitation, to a temperature of from about 45° C. to about 65° C., prior to being poured into stick-form molds.

Care should be taken in the processes of making these compositions to maintain uniform distribution of the particulate materials throughout the antiperspirant sticks. Specific essential and non-essential materials to be included, and their levels, are selected to produce a stick of desired hardness which maintains its dimensional stability while depositing a suitable amount of antiperspirant material on the skin during normal use. Hardness of sticks can be determined by a variety of methods, including American Society for Testing and Materials (ASTM) Method D-5. This method involves the use of a needle of particular weight and dimension, which is permitted to travel downward through the stick material for a pre-determined period of time. The distance traveled by the needle is a relative measure of the stick hardness. Utilizing Method D-5, with a #1554 penetration needle (manufactured by Sergeant-Welch Scientific Company) weighing 50 grams, and a Precision Model 73515 Penetrometer (manufactured by Precision Scientific, a subsidiary of GCA Corporation), the antiperspirant sticks of the present invention preferably yield a penetration of from about 60 to about 200 millimeters, more preferably from about 80 to about 150 millimeters, over a period of 5 seconds.

The low residue antiperspirant stick compositions of the present invention are used in a conventional manner. Specifically, the compositions may be used to prevent and/or control perspiration wetness by topically applying, one or more times a day, an effective amount of the composition to areas of the body particularly prone to perspiration (e.g., the underarm area).

The following non-limiting examples illustrate the compositions, methods of making, and methods of using described in the present application.

EXAMPLE I

An antiperspirant stick composition of the present invention is prepared as follows. All of the ingredients described below are combined and heated to about 82° C. with agitation. The batch is then cooled to about 52° C. and poured into canisters.

| Component | Weight % |
|---|---|
| Cyclomethicone D-5 [1] | 39.8 |
| Light Mineral Oil [2] | 11.5 |
| Dimethicone (50 csk) [3] | 1.5 |
| Stearyl Alcohol | 14.0 |
| Hydrogenated Castor Oil [4] | 4.5 |
| Eicosanol | 0.2 |
| Talc | 1.5 |
| Fumed Silica [5] | 1.0 |
| Aluminum Chlorohydrate [6] | 26.0 |
| | 100% |

[1] A cyclic polydimethylsiloxane containing 5 carbons, supplied by G.E. Silicones
[2] Benol White Mineral Oil, supplied by Witco Chemical Corporation (viscosity = 18–20 csk at 40° C.; density + 0.839–0.855 g/cm$^3$)
[3] Supplied by Dow Corning
[4] Castor Wax MP 80, supplied by NL Industries
[5] Cab-O-Sil HS-5, supplied by Cabot Corporation
[6] Reheis 501 macrospherical aluminum chlorohydrate, supplied by Reheis Chemical Company

EXAMPLE II

The following is an antiperspirant stick composition of the present invention.

| Component | Weight % |
|---|---|
| Cyclomethicone D-5 | 41.8 |
| Permethyl 103A [1] | 16.0 |
| Stearyl Alcohol | 14.0 |
| Hydrogenated Castor Oil | 2.0 |
| Eicosanol | 0.2 |
| Talc | 3.0 |
| Aluminum Zirconium Tetrachlorohydrex Gly [2] | 23.0 |
| | 100% |

[1] 24 carbon branched chain hydrocarbon fluid, supplied by The Permethyl Corporation (density = 0.838 g/cm$^3$; b.p. = 230–350° C.)
[2] Dow Corning AZG-369, supplied by Dow Corning This composition is prepared by essentially the same procedure as described in Example I.

EXAMPLE III

The following is an antiperspirant stick composition of the present invention.

| Component | Weight % |
|---|---|
| Cyclomethicone D-5 | 38.8 |
| Permethyl 104A [1] | 6.0 |
| Permethyl 102A [2] | 6.0 |
| PPG-14-Butyl Ether | 4.0 |
| Stearyl Alcohol | 14.0 |
| Hydrogenated Castor Oil | 5.0 |
| Eicosanol | 0.2 |
| Fumed Silica | 1.0 |
| Aluminum Zirconium Trichlorohydrex Gly [3] | 25.0 |

-continued

| Component | Weight % |
|---|---|
| | 100% |

[1] 68 carbon branched chain hydrocarbon fluid, supplied by Permethyl Corporation (density = 0.89 g/cm$^3$; b.p. = >300° C.)
[2] 20 carbon branched chain hydrocarbon fluid supplied by Permethyl Corporation (density = 0.83 g/cm$^3$; b.p. = 275–300° C.)
[3] supplied by Westwood Chemical Company This stick composition is prepared by essentially the same procedures as described in Example I.

EXAMPLE VI

The following is an antiperspirant stick composition of the present invention.

| Component | Weight % |
|---|---|
| Cyclomethicone D-5 | 42.5 |
| Light Mineral Oil (Benol White) | 14.6 |
| Stearyl Alcohol | 13.6 |
| Hydrogenated Castor Oil | 4.8 |
| Eicosanol | 0.2 |
| Aluminum Chlorohydrate [1] | 24.3 |
| | 100% |

[1] Dow Corning ACH-323 impalpable aluminum chlorohydrate, supplied by Dow Corning This stick composition is prepared by essentially the same procedure as described in Example I.

The antiperspirant compositions described in Examples I-IV, when applied to the axillary area of the user, provide effective prevention and control of perspiration wetness. These compositions have excellent aesthetics and leave little visible white residue on the skin after application.

The following is an experiment which demonstrates the residue benefit of the antiperspirant solids disclosed in this application.

Eight antiperspirant products were made —the four example formulas above and four products with compositions identical to these four examples except that the conventional emollient, cyclomethicone D-5, was substituted for the nonvolatile hydrocarbon emollient component.

The relative visible residue level of each stick was then determined by colorimetric measurement of the white residue deposited on a black vinyl substrate. Specifically, for each sample, a 10.2 cm × 12.7 cm strip of black vinyl (manufactured by Uniroyal) was weighed, and a base colorimetric reading (black-white, or L-axis) was obtained using a Gardner XL-800 Tristimulus Colorimeter at three places on the strip. The antiperspirant stick sample was then evenly applied across the vinyl strip until 0.35 grams of product was deposited. A colorimeter reading was then immediately obtained at three points on the vinyl strip. The average color difference reading ($\Delta L$) was then obtained for each strip by subtracting the average colorimeter reading of the untreated strip from the average reading for the treated strip. (Note that the more positive the $\Delta L$ value, the greater the visible white residue left by the product.)

Each of the eight stick compositions was tested in this manner, on two strips of vinyl per sample. To obtain the drydown residue for each sample, this entire procedure was repeated except that colorimeter readings of the treated swatch were taken six hours after application. The resulting data is given in the following table.

| Product | Residue ($\Delta L$) Initial | 6 Hour Drydown |
|---|---|---|
| Example I | 2.98 | 1.56 |
| Example I w/o nonvolatile hydrocarbon | 5.03 | 16.50 |
| Example II | 1.38 | 1.92 |
| Example II w/o nonvolatile hydrocarbon | 5.57 | 36.16 |
| Example III | 1.34 | 2.05 |
| Example III w/o nonvolatile hydrocarbon | 6.61 | 23.18 |

For each pair of similar products, the initial and the drydown residue values are significantly different at the $\alpha=0.05$ level of significance. These data demonstrate that the nonvolatile hydrocarbon emollient-containing products of this invention exhibit significantly less visible white residue (initially and over time) than do similar products made with the conventional emollient cyclomethicone D-5.

What is claimed is:

1. A suspensoid low residue antiperspirant stick composition, substantially free of water and containing from 0 to about 4% of total particulate materials other than the antiperspirant active, comprising:
   (a) from about 30% to about 70% of a volatile silicone material;
   (b) from about 5% to about 35% of a particulate antiperspirant active;
   (c) from about 3% to about 20% of a non-volatile paraffinic hydrocarbon fluid selected from the group consisting of mineral oils, branched chain hydrocarbons containing an average of from about 20 to about 40 carbon atoms, and mixtures thereof; and
   (d) from about 10% to about 20% of a low melting point wax.

2. A suspensoid low residue antiperspirant stick composition according to claim 1 wherein the antiperspirant active is selected from the group consisting of inorganic and organic salts of aluminum, zirconium and zinc, and mixtures thereof.

3. A suspensoid low residue antiperspirant stick composition according to claim 2 wherein the volatile silicone material is selected from the group consisting of cyclic polydimethylsiloxanes having from about 3 to about 7 silicon atoms, linear polydimethylsiloxanes having from about 3 to about 9 silicon atoms, and mixtures thereof.

4. A suspensoid low residue antiperspirant stick composition according to claim 3 additionally containing from about 1% to about 7% of a high melting point wax.

5. A suspensoid low residue antiperspirant stick composition according to claim 3 wherein the low melting point wax is selected from the group consisting of stearyl alcohol, cetyl alcohol, palmitic acid, myristyl alcohol, paraffin, and mixtures thereof.

6. A suspensoid low residue antiperspirant stick composition according to claim 3 wherein the non-volatile paraffinic hydrocarbon fluid is selected from the group consisting of branched chain hydrocarbons containing an average of from about 20 to about 40 carbon atoms, and mixtures thereof.

7. A suspensoid low residue antiperspirant stick composition according to claim 6 comprising from about 5% to about 15% of the branched chain hydrocarbons.

8. A suspensoid low residue antiperspirant stick composition according to claim 7 wherein the antiperspirant active has the formula $Al_2(OH)_xQ_y \cdot XH_2O$, where Q is selected from the group consisting of chlorine, bromine and iodine, x is from about 2 to about 5, $x+y=$ about 6, and x and y do not need to be integers, and X is from about 1 to about 6.

9. A suspensoid low residue antiperspirant stick composition according to claim 8 wherein the volatile silicone material has the formula

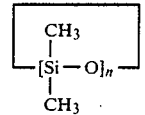

wherein n is from about 3 to about 7.

10. A suspensoid low residue antiperspirant stick composition according to claim 9 comprising from about 35% to about 50% of the volatile silicone material.

11. A method for preventing and controlling perspiration wetness in humans comprising the application to the underarm area of an effective amount of the suspensoid low residue antiperspirant stick composition according to claim 1.

* * * * *

UNITED STATES PATENT AND TRADEMARK OFFICE
CERTIFICATE OF CORRECTION

PATENT NO.  : 4,985,238

DATED       : January 15, 1991

INVENTOR(S) : Paul R. Tanner; Randolph G. Nunn, Jr.; John P. Luebbe

It is certified that error appears in the above-identified patent and that said Letters Patent is hereby corrected as shown below:

Column 10, line 13 insert:

| | | |
|---|---|---|
| Example IV | 0.99 | 1.20 |
| Example IV w/o nonvolatile hydrocarbon | 4.23 | 22.79 |

Signed and Sealed this

Twenty-eighth Day of June, 1994

BRUCE LEHMAN

Attest:

Attesting Officer

Commissioner of Patents and Trademarks